United States Patent [19]

Wood et al.

[11] 3,959,278
[45] May 25, 1976

[54] METHOD OF SYNTHESIS OF PTERIDINES

[75] Inventors: Hamish Christopher Swan Wood, Glasgow, Scotland; Alexander Stuart, Bromley; Adrian Charles Ward Curran, Harrow, both of England; Saieba Al-Hassan, Baghdad, Iraq

[73] Assignee: Burroughs Wellcome Co., Research Triangle Park, N.C.

[22] Filed: Feb. 14, 1974

[21] Appl. No.: 442,494

Related U.S. Application Data

[62] Division of Ser. No. 162,297, July 13, 1971, Pat. No. 3,810,893.

[30] Foreign Application Priority Data

July 27, 1970 United Kingdom............... 36289/70

[52] U.S. Cl. ............................................. 260/251.5
[51] Int. Cl.² ...................................... C07D 475/04
[58] Field of Search ................................. 260/251.5

[56] References Cited
UNITED STATES PATENTS

| | | | |
|---|---|---|---|
| 3,635,978 | 1/1972 | Wood et al. ................. | 260/256.4 C |
| 3,725,408 | 4/1973 | Wood et al. ................. | 260/251.5 |

OTHER PUBLICATIONS

Pfleiderer et al., C.A. 65, 20126e, (1966).
Gilman – "Organic Chemistry" – Vol. 1 – 2nd Edition – Wiley Press, (1938), p. 660.

*Primary Examiner*—Raymond V. Rush
*Attorney, Agent, or Firm*—Donald Brown

[57] ABSTRACT

A pharmaceutical formulation of a compound of formula (II')

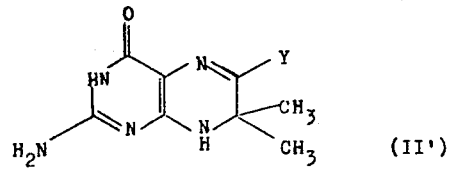

wherein Y is a lower alkyl group, in association with a pharmaceutically acceptable carrier, as an antibacterial product, and methods involving the preparation and reductive cyclization of a compound of formula (IV)

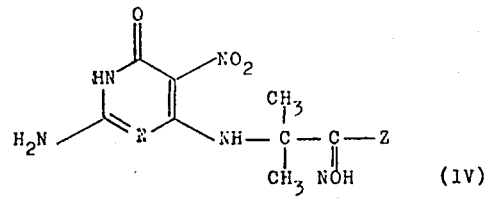

wherein X is a lower alkyl group or a hydroxymethyl group.

6 Claims, No Drawings

METHOD OF SYNTHESIS OF PTERIDINES

This is a division of application Ser. No. 162,297, filed on July 13, 1971, now U.S. Pat. No. 3,810,893.

The present invention relates to pteridine derivatives, methods of preparing them and to their use in pharmaceutical formulations.

It is already established that the compound 2-amino-4-hydroxy-6-hydroxymethyl-7,7-dimethyl-7,8-dihydropteridine of formula (I) or its tautomers or pharmaceutically acceptable salts thereof, has bacteriostatic activity, being particularly effective against *Cl. perfringens* and *Derm. dermatonomous*.

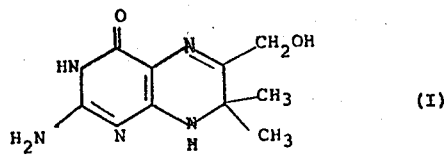

It has now been found that the compounds represented by the following formula (II') or their tautomers or pharmaceutically acceptable salts thereof,

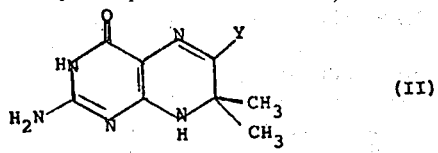

wherein Y is a lower alkyl group, preferably one which contains a methylenic group ($-CH_2$) attached to the ring system, are also useful as bacteriostats or in antibacterial products. For instance they produce substantial inhibition of the dihydrofolate synthesis upon which bacteria, such as *E. coli*, are dependent for their growth, indicating general antagonism of bacterial metabolic processes.

As used herein and throughout the specification, the term "lower alkyl group" refers to a straight or branched chain alkyl group having 1 to 4 carbon atoms.

The compound wherein Y is a methyl group is especially preferred.

A compound of formula (II'), or its salt, may also be used in in vitro pharmacological investigations in clinical and diagnostic tests establishing, for instance, the properties of bacteria. When used as a bacteriostat, it is present in a concentration of 110 to 180 mg of base/ml. of the solution in which the organism grows in the absence of the compound. A further use of a compound (II'), when in solution, is in the treatment of wounds, for example after surgery, to prevent the growth of bacteria.

If a salt of the compound (II') is used in in vitro or in vivo conditions, the salt should be a salt of pharmaceutically acceptable acid or alkali, such as hydrochloric acid, sulphuric acid, tartaric acid, maleic acid, ammonia, sodium hydroxide and tetramethyl ammonium hydroxide.

According to one aspect of the present invention there are provided pharmaceutical formulations comprising the compound (II') or tautomeric forms thereof, or pharmaceutically acceptable salts thereof, in association with a pharmaceutically acceptable carrier.

The substance may be presented advantageously in discrete units, such as tablets, capsules, cachets or ampoules, each containing a predetermined amount of the compound. It may also be presented as a powder or granules, as a solution or suspension in an aqueous or non-aqueous (optionally emulsified) liquid, or as an ointment. For parenteral use, the formulations must be sterile and are presented in sealed containers. The formulations of this invention may be made by any of the methods of pharmacy, and may include one or more of the following accessory ingredients: diluents, solutes, buffers, flavouring, binding, dispersing, surface-active, thickening, lubricating and coating materials, preservatives, antioxidants, and ointment bases, and any other acceptable excipients.

The above-mentioned lowest member of the group of compounds (II'), the 6-methyl-substituted compound, has been prepared according to the method described by Pfleiderer and Zondler (Chem. Ber. 1966, 99, 3008), in which 3-amino-3-methylbutan-2-one hydriodide is reacted with 2-amino-4-chloro-6-hydroxy-5-nitropyrimidine and the product reductively cyclised. However the preparation of the amino ketone is cumbersome, involving the formation of an undesirable and potentially explosive azide intermediate derivative. The amino ketone preparation is therefore expensive, and the final stages of the entire process are unsatisfactory in many respects, in particular the amino ketone undergoes self condensation and a number of side products are produced, with concomitant low yield of the desired pteridine.

A much improved method of synthesis of the compounds of formula (II),

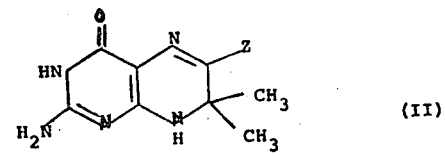

wherein Z is a lower alkyl group, preferably one which contains a methylenic group attached to the ring system, or a hydroxymethyl group, has now been discovered which uses the intermediate of formula (IV) or, going one stage further back, that of formula (V). The compounds (II) can therefore be prepared according to the following reaction sequence:

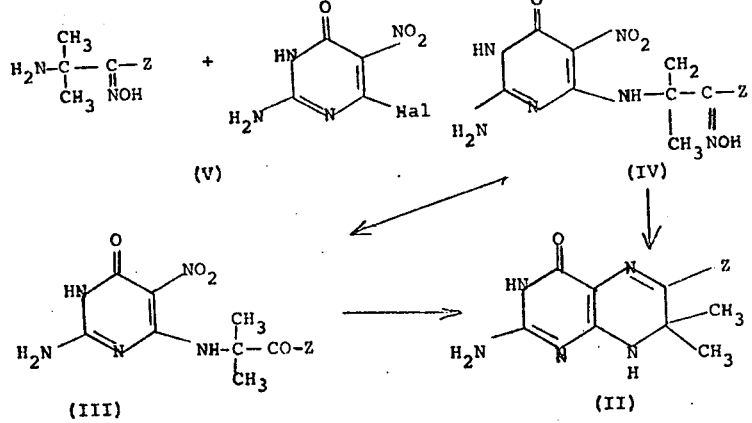

The compounds of formula (IV) are all novel and those of formula (V) are novel, except when Z is a methyl group, and these therefore form further aspects of the present invention.

The conversion of compound (IV) to compound (II) is carried out most advantageously in practice by effecting reductive cyclisation of the former. This may be achieved by the use of reducing agents which are capable of reducing the nitro group without attacking other parts of the molecule; for example it may be achieved readily by means of catalytic hydrogenation using catalysts such as palladium charcoal, platinum, or Raney nickel, but reduction with sodium dithionite is especially preferred. This latter reagent is cheap, effects a rapid reaction and does not require a source of hydrogen as do the catalytic reagents. The reductive cyclisation may be carried out under a variety of conditions, the pH of the medium required depending on the choice of reducing agent. An alkaline medium is preferred for reduction with sodium dithionite and also for hydrogenation using Raney nickel.

Another manner of carrying out the above reductive cyclisation to prepare compound (II) proceeds through the isolation of the ketonic intermediate of formula (III), which may be purified by methods known in the art, e.g. by recrystallisation, by reaction of compound (IV) with an acid, preferably a moderately strong acid. The acid may be, for example, an organic acid such as trifluoroacetic or benzenesulphonic or a mineral acid, especially a dilute mineral acid, such as hydrochloric or sulphuric acid. The compound (III) is then reductively cyclised to compound (II) as hereinbefore described for compound (IV), the reaction most probably passing through the diamino pyrimidine intermediate.

Preparation of the novel pyrimidine ketoxime (IV) is readily effected by reacting the compound of formula (V) or a salt thereof with readily-available 2-amino-4-halogeno-6-hydroxy-5-nitro pyrimidine. The halogeno substitutent is a bromine, iodine or fluorine atom or most preferably a chlorine atom, and an acid addition salt of the compound (V) may conveniently be a hydrohalide, preferably the hydrochloride. The reaction is desirably effected in the presence of an acid binding agent such as a weak base, for example sodium carbonate, sodium acetate, or in particular a tertiary amine, such as triethylamine.

The compound (V) or a salt thereof can be prepared by reacting a nitroso halide, for practical purposes most preferably the chloride, of formula (VI) with ammonia solution. Conveniently ammonia gas is bubbled through the reaction solvent, which may be an alkanol such as methanol, thereby preventing any precipitation during the process. The compound (VI) can in turn be prepared by an addition reaction with the appropriate nitrosyl halide, e.g. nitrosyl chloride. The reagent may be available commercially or could conveniently be prepared in situ, for instance, from a nitrosating agent with a concentrated hydrohalic acid. Suitable nitrosating agents include isoamyl nitrite and methyl nitrite.

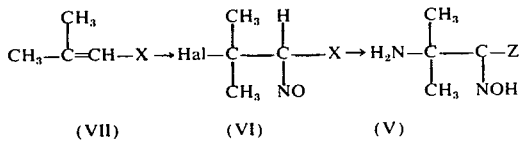

(VII)   (VI)   (V)

In formulae (VII) and (VI), the definition of X is the same as that defined herein for Z, except that X may also be an ester group, such as an acyl ester $CH_2O.CO.R$, where R is a lower alkyl group. The sequence (VII) to (V) is especially applicable when X is a hydroxymethyl group.

The intermediates of formula (VI) are novel compounds, except when X is a methyl group, and form yet a further aspect of the present invention.

There are many ways of preparing compound (VII) wherein X is a hydroxymethyl group or an ester thereof, but it has been found advantageous and convenient to proceed:

(a) when X is hydroxymethyl (VII')
  either (i) by reduction of the corresponding acid (IX) with a powerful reducing agent, especially an organo metallic hydride, such as lithium aluminiumhydride, or preferably sodium dihydro-bis-2-methoxyethoxy aluminate; or
  (ii) by structural rearrangement of 3-methyl-3-hydroxybut-1-ene of formula (VIII) to the thermodynamically more stable alcohol of formula (VII'), for example by means of boric acid;

(b) when X is an acyl ester group, such as —$CH_2O.CO.R$.
  either (i) by reaction of the alcohol of formula (VII') with the appropriate acid anhydride; or
  (ii) from 3-methyl-3-hydroxybut-1-ene (VIII) by structural rearrangement, as described under (a) (ii), in the presence of the appropriate organic acid go give Compound (VII'')

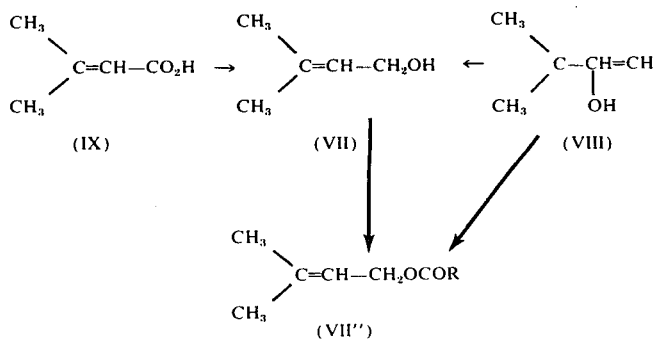

Compound (VII'') may then be converted with a nitrosating agent, as hereinbefore defined, to the nitrosohalide of formula (VI), which may be further reacted to give the compound of formula (V) or a salt thereof, where Z is a hydroxymethyl group. The sequence (VIII) to (VII'') to (VI) is especially preferred for the initial stages of the synthesis.

The compound of formula (V) or a salt thereof may also be prepared from the corresponding ketone of formula (X) or a salt thereof, wherein Y is a lower alkyl group, preferably one which contains a methylenic group attached to the ring system, by reaction with hydroxylamine or an acid salt thereof. Advantageously at least one equivalent of sodium acetate, sodium carbonate or triethylamine is present to act as an acid binding agent.

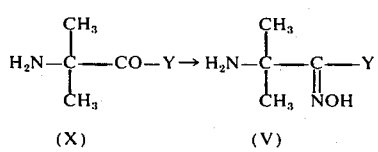

Compound (X) may itself be prepared, for example, according to the following reaction scheme:

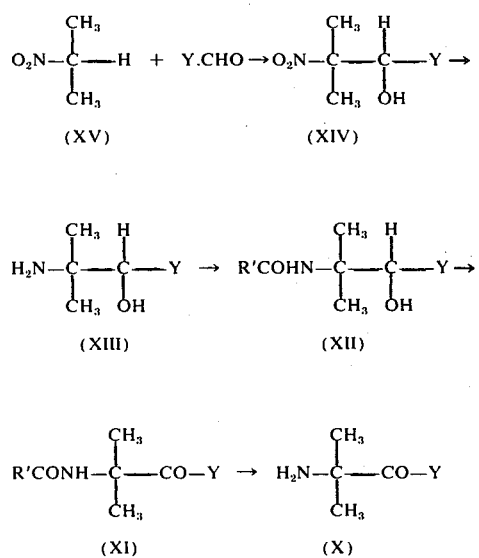

wherein $R^1$ is an alkyl, aryl or aralkyl group.

Nitropropane, which is readily available, is condensed with the appropriate aldehyde of formula (XV) in the presence of a strong basic catalyst such as an alkali metal hydroxide or alkoxide. The product (XIV) is reduced, for example by catalytic hydrogenation, preferably using Raney nickel, to compound (XIII), the amino group is protected to give compound (XII), the hydroxyl group is oxidised, for example using chromium trioxide in pyridine, to produce compound (XI), and finally the protecting group is removed by hydrolysis, conveniently using a mineral acid. The protection of the amino group is readily achieved using an acyl group, such as a benzoyl, acetyl or carbobenzoxy group, preferably the benzoyl group.

According to the present invention in further aspects there are also provided:

1. The methods described herein for preparing any of the compounds of formula (II), comprising effecting reductive cyclisation of compounds of formula (IV).
2. The methods described herein for preparing any of the compounds (IV) from (V), (V) from (VI) or (VII), (V) from (X) and (X) from (XIII).
3. Compounds of formula (II), (IV), (V), (VI) and (X), whenever prepared by a method as defined under (1), (2) or (3), respectively.
4. As novel compounds of value as chemical intermediates:

Compounds of formula (XI), as hereinbefore defined, especially 3-N-benzoylamino-3-methylbutan-2-one.

The following Examples illustrate the invention but are in no way intended to limit the scope of the invention.

Temperatures are in degrees Celsius.

EXAMPLE 1

Synthesis of Compounds of Formula (V)

3,3-dimethyl allyl alcohol (VII') (X=CH$_2$OH)

(a) A solution of 3,3-dimethylacrylic acid (20 g., 0.2M) in sodium-dried ether (200 ml.) was treated dropwise with 64 g. (0.2M+10%) of a 70% solution of sodium dihydro-bis (2-methoxyethoxy) aluminate in benzene, the temperature being maintained at 0° until the addition was complete (about 1 hour). The reaction mixture was stirred for five hours at room temperature, and water was then added slowly. The sodium aluminate which precipitated was filtered off, and the filtrate was extracted with ether (4 × 100 ml.) The combined extracts were dried, the solvent was removed, and the residual oil was distilled to give 3,3-dimethylallyl alcohol as a colourless liquid b.p. 54°-55°/25 mm Hg. or (b) A mixture of 3-methyl-3-hydroxybut-1-ene (64 g.) and boric acid (60 g.) was stirred at 110°C in an apparatus equipped for distillation. The substituted butene distilled of gradually over 5 hours and was replaced with a fresh supply at intervals throughout the 5 hours. The cooled reaction mixture was diluted with water, neutralised with solid sodium carbonate and extracted with ether. The ethereal extracts were brine washed, dried and evaporated and the residual oil distilled (13 g.) 50–60/14 mm Hg.

2. 3,3-dimethyl alkyl acetate (VII'') (X=CH$_2$O.CO.CH$_3$)

(a) 3,3-Dimethylallyl alcohol (4.3 g., 0.05 M) and acetic anhydride (6.5 g., 0.07 M) were heated on a steam bath for 1 hour and then distilled from the same flask at water pump pressure. The total distillate was poured onto ice-water and the pH adjusted to 7.0 with sodium hydroxide, under ether. The ethereal layer was removed and the aqueous solution extracted with ether (2 × 20 ml.). The combined extracts were washed with brine, dried and the solvent removed to give a pale yellow oil. Fractional distillation gave the 3,3 dimethylallyl acetate as a colourless oil (3.5 g.) b.p. 40°–43°/20 mm Hg. or (b) A mixture of 3-methyl-3-hydroxybut-1-ene (32 g.), acetic acid (150 ml.) and boric acid (30 g.) was stirred at 105° for 4 hours. The cooled reaction mixture was diluted with water, neutralised with solid sodium carbonate and extracted with ether (3 × 50 ml.) The combined ethereal extracts were brine washed, dried and the solvent removed giving a pale yellow oil (30 g.) Distillation gave 3,3-dimethylallyl acetate as a colourless oil (22 g.) b.p. 44°–45°/14 mm Hg.

3. 3-chloro-3-methyl-2-nitrosobutan-1-ol (VI) (X=CH$_2$OH)

3,3-Dimethylallyl alcohol (50 ml), iso-amyl nitrite (70 ml.) and glacial acetic acid (100 ml.) were cooled in an ice-salt bath and treated with ice-cold concentrated hydrochloric acid (40 ml) added dropwise with stirring. Glacial acetic acid (40 ml) was added slowly maintaining the temperature at 0°–5°. Towards the end of the addition a white solid precipitated. The reaction mixture was then stirred at 0° for a further 30 minutes and cooled in an acetone/CO$_2$ bath for 15 minutes. The product was filtered through a large precooled Buchner funnel and washed with a little cold benzene and dried. Recrystallisation from dioxan gave the desired nitrosobutanol as colourless needles (19 g.) m.p. 119°.

4. 3-chloro-3-methyl-2-nitroso-1-butyl acetate (VI) (X=CH$_2$O.CO.CH$_3$)

3,3-Dimethylallyl acetate (25 ml.), iso-amyl nitrite (45 ml.) and glacial acetic acid (65 ml.) were cooled in an ice-salt mixture. An ice-cold mixture of concentrated hydrochloric acid (20 ml.) and glacial acetic acid (20 ml.) was added gradually with stirring. The solution became green and towards the end of the addition a white solid precipitated. The solid was collected by filtration and dried (13 g.) Recrystallisation from CCl$_4$ — 40°/60° petrol gave the title compound as colourless needles (10 g.) m.p. 117°–119°.

5. 3-chloro-3-methyl-2-nitrosobutane (VI) (X=CH$_3$)

A mixture of 2-methylbut-2-ene (70 g.) and iso-amyl nitrite (100 ml.) was stirred in an ice-salt bath for 30 minutes and then concentrated hydrochloric acid (100 ml.) was added dropwise with stirring at such a rate as to keep the temperature below 5° (~1 hour) A blue solution was obtained, and a crystalline paste gradually formed. The reaction mixture was stirred for a further 30 minutes below 5°C, followed by cooling in an acetone/CO$_2$ bath for fifteen minutes. The pale blue precipitate was filtered and washed with ice-cold ethanol (50 ml.) The product was dried in a stream of air until all traces of blue colour had gone, leaving the title compound as colourless crystals (60g.) m.p. 75°.

6. 3-amino-3-methyl-2-hydroxyiminobutan-1-ol hydrochloride (salt of V) (Z=CH$_2$OH)

(a) 3-Chloro-3-methyl-2-nitrosobutan-1-ol (10 g.) was dissolved in dry methanol (200 ml.) saturated with ammonia at 0°. The mixture was then left overnight at room temperature and evaporated to dryness in vacuo at room temperature. The residue was extracted with hot dry benzene (200 ml.) and the benzene-insoluble component extracted further with hot secondary butanol (220 ml.). The secondary butanol extract was evaporated to small volume and the product precipitated by dropwise addition of ether. This was filtered and dried in vacuo (7.5g.)m.p. 172°–173°. 1 or (b) 3-Chloro-3-methyl-2-nitroso-1-butyl acetate (5 g.) was treated with a methanolic ammonia solution (15 ml) and the mixture stirred at room temperature in a sealed flask for 2 days. Removal of the volatile material gave an oily solid which was triturated with ethanol and the soluble component retained. Removal of the ethanol gave a residual solid which was triturated with hot acetone giving a creamy white powder (4 g.) m.p. 178°–179°

7. 3-amino-3-methylbutan-2-one oxime hydrochloride (Salt of V) (Z=CH$_3$)

3-Chloro-3-methyl-2-nitrosobutane (60 g.) was added portionwise to dry methanol (600 ml.) saturated with ammonia at 0°. The solution was left at room temperature for 5 hours then refluxed for 16 hours in the presence of a stream of dry ammonia. The mixture was evaporated to dryness in vacuo at room temperature and the residue extracted with hot dry benzene (900 ml.) followed by boiling secondary butanol (1300 ml.). The secondary butanol extract was evaporated in vacuo at room temperature to a thick slurry. This was cooled, filtered and dried in vacuo (56 g.) m.p. 190° (decomp).

EXAMPLE 2

Alternative Synthesis of Compounds of Formula (V)

1. 3-nitro-3-methylbutan-2-ol (XIV) (Y=CH$_3$)

Freshly distilled acetaldehyde (27.3 g., 0.62 M) was added portionwise to a well stirred solution of 2-nitropropane (52.08 g. 0.62 M) in 85% ethanol (30 ml.) and 10N sodium hydroxide (1.2 ml.), maintaining the reaction temperature at 30°–35°. After two-thirds of the aldehyde had been added, a further 1.2 ml. of 10N sodium hydroxide and 8 ml. of water was added followed by the remaining acetaldehyde, and the mixture stirred at room temperature for 4 days. Excess acetaldehyde and 2-nitropropane were removed at the water pump. The residue was dissolved in water (100ml.) and extracted with ether (3 × 50ml.). The combined ethereal extracts were brine washed, dried and distilled to give the title compound as a colourless oil (26g) b.p. 82°–83°/14 mm Hg.

2. 3-amino-3-methylbutan-2-ol (XIII) (Y=CH$_3$)

3-Nitro-3-methylbutan-2-ol (5g.,0.035 M) was dissolved in methanol (300 ml.) and hydrogenated over freshly prepared Raney nickel (~2g) at room temperature and 4 atmospheres pressure for 5 hours until there was no further visible uptake of hydrogen. The nickel catalyst was removed by filtration and the solvent evaporated to give the title compound as a colourless oil (3.6g).

3. 3-N-benzoylamino-3-methylbutan-2-ol (XII) (Y=CH$_3$)

3-Amino-3-methylbutan-2-ol (6.1 g.) was dissolved in benzene (120 ml.), treated with anhydrous sodium carbonate (16 g.) and cooled to 10°. The mixture was then treated with benzoychloride (9.2 g.) in benzene (30 ml.) at 10° and left to stand at this temperature for 3 hours. After a further 2 hours at room temperature the reaction mixture was refluxed for 30 minutes, filtered hot and the solid extracted with hot benzene (2 × 100 ml.) The combined filtrates were evaporated to 100 ml. and cooled. The colourless crystalline solid was collected and recrystallised from benzene as colourless needles (5 g.) m.p. 118°–120°

4. 3-N-benzoylamino-3-methylbutan-2-one (XI) (Y=CH₃)

3-N-Benzoylamino-3-methylbutan-2-ol (2.02g., 0.1 M) in anhydrous pyridine (4 ml.) was added to the oxidising reagent, prepared by adding chromium trioxide (3 g., 0.03 M) to a vigorously stirred, cooled solution of pyridine (35 ml.) over 15 minutes. The mixture was stirred at 0° for 30 minutes and then at room temperature for 22 hours. The reaction mixture was poured onto water (100 ml.) and extracted with ether (3 × 50 ml.) The combined extracts were washed with brine, dried and evaporated to give a white powder, which recrystallised from benzene-petrol as colourless needles (1.6g) m.p. 124°–125°.

5. 3-amino-3-methylbutan-2-one-hydrochloride (Salt of X) (Y=CH₃)

3-N-Benzoylamino-3-methylbutan-2-one (1 g.) was suspended in 20% hydrochloric acid (10 ml.), refluxed for 8 hours, cooled and the precipitated benzoic acid filtered. The filtrate was evaporated and the residue treated with water (2 ml.) and filtered to remove a further quantity of benzoic acid. The resultant filtrate was evaporated and the residue triturated with cold ethanol (3 × 5 ml.) filtering, evaporating the filtrate and discarding the solid each time. The resultant residue was recrystallised from ethanol-ether as colourless needles (500 mg.) m.p. 212°–214°.

This was then reacted with hydroxylamine in the presence of triethylamine to give 3-amino-3-methylbutan-2-one oxime hydrochloride (Salt of V) (Y=CH₃).

EXAMPLE 3

Synthesis of Compounds of Formula (II)

1. 2-amino-4-chloro-6-hydroxy-5-nitropyrimidine

2-Amino-4-chloro-6-hydroxypyrimidine (7.5 g.) was dried over P₂O₅ at 0.5 mmHg for 2 hours, partially dissolved in concentrated sulphuric acid (9 ml.) and the slurry cooled to 0°C and treated portionwise with fuming nitric acid (8 ml.) with constant stirring. The yellow solution was stirred for an additional 30 minutes at room temperature and then poured onto ice (30 g.). The pale yellow solid was filtered, washed with ice-water and then ether and dried over P₂O₅ at 0.5 mmHg giving the title compound as a pale yellow solid (8.32 g.) m.p. 260° (decomp.)

2. 2-amino-4-(1',1'-dimethyl-3'-hydroxyacetonyl)amino-6-hydroxy-5-nitro pyrimidine oxime (IV) (Z=CH₂OH)

3-Amino-3-methyl--3-hydroxyiminobutan -1-ol hydrochloride (2.5 g.) was dissolved in ethanol (16 ml.) and treated with 2-amino-4-chloro-6-hydroxy-5-nitropyrimidine (2.8 g) and triethylamine (2.8 g.), and the mixture stirred at room temperature for 2 hours, at reflux for 4 hours and at room temperature for a further 8 hours. The reaction mixture was heated, filtered hot and the solid washed with hot ethanol. The ethanol was removed from the combined filtrates giving a pale yellow powder which was triturated with small amounts of ethanol. The powder was recrystallised from boiling water to give the title compound as an off-white powder (1.5 g).

3. 2-amino-4-(1',1'-dimethylacetonyl)amino-6-hydroxy-5-nitro-pyrimidine oxime (IV) (Z=CH₃)

3-Amino-3-methylbutan-2-one oxime hyrochloride (5 g.), 2-amino-4-chloro-6-hydroxy-5 nitro pyrimidine (6 g.) and triethylamine (10 ml.) were refluxed in ethanol (200 ml.) for 16 hours. The reaction mixture was cooled and the white preceipitate was collected and purified by dissolving in 2N-ammonium hydroxide solution. Reprecipitation with glacial acetic acid gave the pyrimidinylamino-ketone oxime as a white solid (6.0 g.) m.p. 260° (decomp).

4. 2-amino-4-(1',1'-dimethyl-3'-hydroxyacetonyl)amino-6-hydroxy-5-nitro pyrimidine (III) (Z=CH₂OH)

2-Amino-4-(1',1'-dimethyl-3'-hydroxyacetonyl-)amino-6-hydroxy-5-nitro pyrimidine oxime (2 g.) was dissolved in 2N hydrochloric acid (200 ml.) and the solution heated on a steam bath for 2 hours. The reaction mixture was concentrated by rotary evaporation at 0.5 mm Hg. at 40° and the resultant solid triturated with acetone, filtered and dried. The yellow powder was recrystallised from boiling water as an off-white powder (1.5 g).

5. 2-amino-4-(1',1'-dimethylacetonyl)amino-6-hydroxy-5-nitro pyrimidine (III) (Z=CH₃)

2-Amino-4-(1',1'-dimethylacetonyl)amino-6-hydroxy-5-nitro-pyrimidine oxime (6.0 g.) was hydrolysed by refluxing for 10 minutes with 2N-hydrochloric acid. The reaction mixture was cooled, filtered and neutralised with 0.880 ammonium hydroxide to precipitate the pyrimidinylamino-ketone as a colourless crystalline solid (5.0 g.) m.p. 289°.

6. 2-amino-4-hydroxy-6-hydroxymethyl-7,7-dimethyl-7,8-dihydropteridine (II) (Z=CH₂OH)

2-Amino-4-(1',1'-dimethyl-3'-hydroxyacetonyl-)amino-6-hydroxy-5-nitropyrimidine (4 g.) was suspended in water (50 ml.), heated on the steambath, and treated with solid sodium dithionite until the original solid had dissolved. After 5-10 minutes the solution was cooled, whereupon the off-white product began to separate out. This was completed by the addition of 0.880 ammonia to pH 8.5–9.0 (2.1 g) m.p. > 300°.

In another experiment the pyrimidinylamino ketone was dissolved initially in 0.1N sodium hydroxide followed by portionwise addition of sodium dithionite and isolation of the product (1.6 g.).

7. 2-amino-4-hydroxy-7-8-dihydro-6,7,7-trimethylpteridine (II) (Z=CH₃)

2-Amino-4-(1',1'-dimethylacetonylamino)-6 hydroxy-5-nitropyrimidine (2 g.) was dissolved in dilute ammonium hydroxide, the solution warmed gently and soldium dithionite added portionwise until a colourless solution was obtained. The pH was adjusted to 7 with acetic acid and the dihydropteridine which precipitated was filtered and washed with water, ethanol and ether (1.75 g.) m.p. 298°–300°.

8. 2-amino-4-hydroxy-6-hydroxymethyl-7,7-dimethyl-7,8-dihydropteridine (II) (Z=CH₂OH)

Direct Method

2-Amino-4- (1',1'-dimethyl-3'-hydroxyacetonyl)amino-6-hydroxy-5-nitro pyrimidine oxime (50 mg.) was dissolved in 0.1N sodium hydroxide (3 ml.) with warming on a steam bath. The warm solution was treated portionwise with sodium dithionite until the yellow colour was dicharged. On cooling a white solid precipitated which was washed with water and dried giving the title compound as a pale yellow powder (40 mg.)

9. 2-amino-4-hydroxy-7,8-dihydro-6,7,7-trimethyl pteridine (II) (Z=CH₃)

Direct Method

2-Amino-4-(1',1'-dimethylacetonylamino)-6-hydroxy-5-nitropyrimidine oxime (50 mg.) was dissolved in 0.1N sodium hydroxide (3 ml.) with warming on the steam bath. The warm solution was treated with sodium dithionite until the yellow colour was discharged. This was collected, washed with water and dried to give the title compound as a pale yellow powder (35 mg.).

EXAMPLE 4

Tablet containing a compound. (II')

| a | Ingredients | |
|---|---|---|
| | 2-Amino-4-hydroxy-7,8-dihydro-6,7,7-trimethylpteridine (II') | 500 mg |
| | Microcrystalline cellulose | 100 mg |
| | Starch | 40 mg |
| | Magnesium stearate | 10 mg |
| | Methylhydroxyethylcellulose | 3 mg |
| | | 653 mg | b. Procedure

The pteridine (II'), microcrystalline cellulose and starch were granulated with a solution of the methylhydroxyethylcellulose in 50% aqueous ethyl alcohol. The magnesium stearate was added to the dried granules, and the whole then compressed.

EXAMPLE 5

Ointment containing a compound (II')

| a | Ingredients | |
|---|---|---|
| | 2-Amino-4-hydroxy-7,8-dihydro-6,7,7-trimethylpteridine (II') | 2 g. |
| | White soft paraffin | 100 g. | b. Procedure

The pteridine (II') was incorporated in part of the white soft paraffin which had been softened by heat. The rest of the white soft paraffin was added, and the whole throughly mixed.

What we claim is:

1. A method of preparing a compound of formula (II)

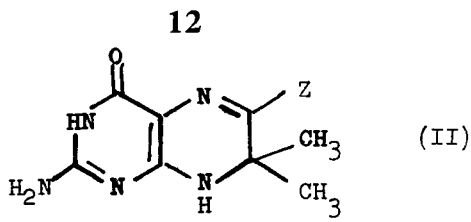

comprising the step of effecting reductive cyclisation of a compound of formula (IV)

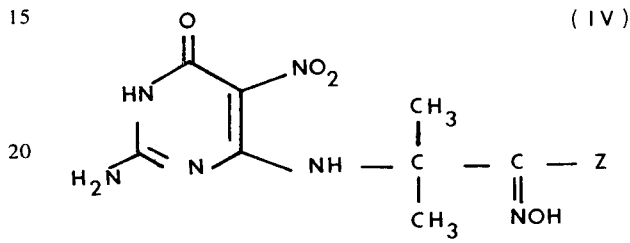

wherein Z is lower alkyl or hydroxymethyl and wherein said reductive cyclisation is carried out by catalytic hydrogenation using palladium on charcoal, platinum or Raney nickel as the catalyst, or by reduction with sodium dithionite.

2. A method of preparing a compound of formula (II),

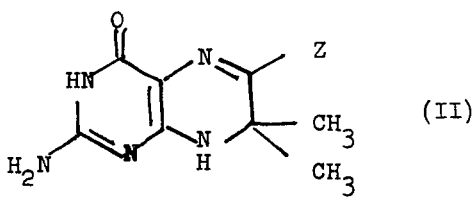

comprising the step of effecting reductive cyclisation of a compound of formula (IV),

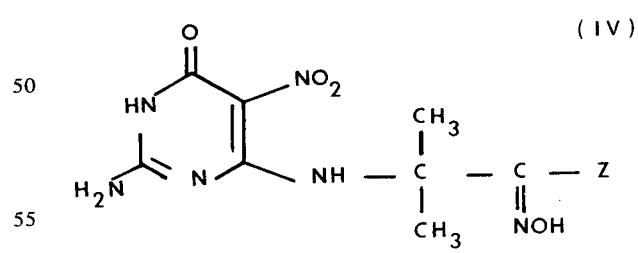

wherein Z is lower alkyl, having — CH₂— attached to the ring system, or hydroxymethyl, and wherein said reductive cyclisation is carried out by catalytic hydrogenation using palladium on charcoal, platinum or Raney nickel as the catalyst, or by reduction with sodium dithionite.

3. A method as claimed in claim 1, wherein the compound of formula (II) is 2-amino-4-hydroxy-6-methyl-7,7-dimethyl-7,8-dihydropteridine.

4. A method as claimed in claim 1, wherein the compound of formula (II) is 2-amino-4-hydroxy-6-hydroxymethyl-7,7-dimethyl-7,8-dihydropteridine.

5. A method of preparing a compound of formula (II)

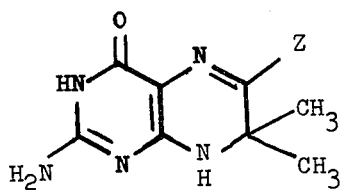
(II)

comprising the step of effecting reductive cyclisation of a compound of formula (IV)

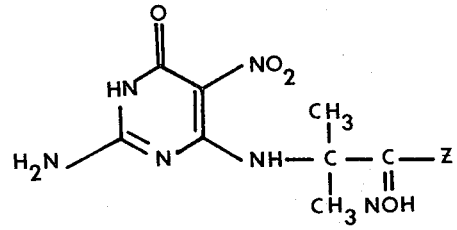

wherein the reductive cyclisation is carried out with sodium dithionite, wherein Z is lower alkyl or hydroxymethyl.

6. A method of preparing a compound of formula (II)

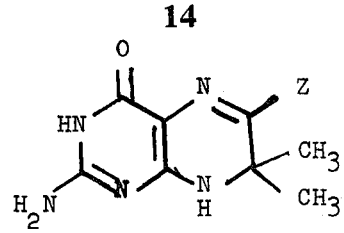
(II)

comprising the step of effecting reductive cyclisation of a compound of formula (IV)

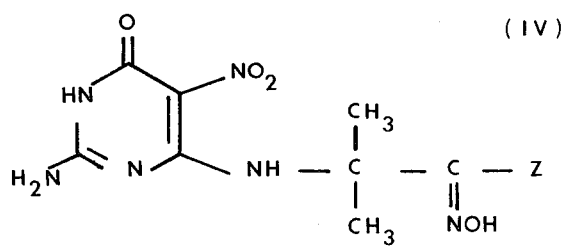
(IV)

wherein Z is lower alkyl or hydroxymethyl, wherein the reductive cyclisation is carried out by catalytic hydrogenation and wherein the catalyst is palladium on charcoal.

* * * * *